(12) United States Patent
Watanabe et al.

(10) Patent No.: US 10,898,877 B2
(45) Date of Patent: *Jan. 26, 2021

(54) SEPARATION MATERIAL

(71) Applicant: Hitachi Chemical Company, LTD., Tokyo (JP)

(72) Inventors: Masaru Watanabe, Tokyo (JP); Yasushi Gotoh, Tokyo (JP); Michio Butsugan, Hitachi (JP); Ryoichi Nakanishi, Tokyo (JP)

(73) Assignee: Showa Denko Materials Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/544,434

(22) PCT Filed: Jan. 19, 2016

(86) PCT No.: PCT/JP2016/051460
§ 371 (c)(1),
(2) Date: Jul. 18, 2017

(87) PCT Pub. No.: WO2016/117567
PCT Pub. Date: Jul. 28, 2016

(65) Prior Publication Data
US 2018/0264435 A1    Sep. 20, 2018

(30) Foreign Application Priority Data

Jan. 19, 2015  (JP) .................. 2015-007776

(51) Int. Cl.
*B01J 20/24* (2006.01)
*G01N 30/88* (2006.01)
*B01J 20/28* (2006.01)
*B01J 20/32* (2006.01)
(Continued)

(52) U.S. Cl.
CPC .............. *B01J 20/24* (2013.01); *B01D 15/08* (2013.01); *B01J 20/28* (2013.01); *B01J 20/286* (2013.01);
(Continued)

(58) Field of Classification Search
None
See application file for complete search history.

(56) References Cited

U.S. PATENT DOCUMENTS 3,966,489 A    6/1976   Barrett et al.
4,965,289 A   10/1990   Sherrington et al.
(Continued)

FOREIGN PATENT DOCUMENTS

EP    2545989 A1    1/2013
JP    S60-169427 A  9/1985
(Continued)

OTHER PUBLICATIONS

Zhou, W. Q.; Gu, T. Y.; Su, Z. G.; Ma, G. H. Polymer 2007, 48, 1981-1988.*
(Continued)

*Primary Examiner* — Krishnan S Menon
(74) *Attorney, Agent, or Firm* — Fitch, Even, Tabin & Flannery, LLP

(57) ABSTRACT

The present invention provides a separation material including porous polymer particles that comprise at least one of styrene and divinylbenzene as a monomer unit at a proportion of 90% by mass or more based on the total amount of the monomers; and a coating layer that comprises a macromolecule having hydroxyl groups and covers at least a portion of the surface of the porous polymer particles, wherein the coating amount provided by the coating layer is 1 to 15 mg/m² per unit specific surface area of the porous polymer particles.

10 Claims, 1 Drawing Sheet

(51) Int. Cl.
*B01J 20/286* (2006.01)
*B01D 15/08* (2006.01)
*C07K 1/16* (2006.01)

(52) U.S. Cl.
CPC ... *B01J 20/28047* (2013.01); *B01J 20/28057* (2013.01); *B01J 20/28097* (2013.01); *B01J 20/321* (2013.01); *B01J 20/3274* (2013.01); *B01J 20/3282* (2013.01); *G01N 30/88* (2013.01); *C07K 1/16* (2013.01)

(56) References Cited

U.S. PATENT DOCUMENTS

| 5,114,577 A | 5/1992 | Kusano et al. | |
|---|---|---|---|
| 2005/0065282 A1* | 3/2005 | Ihre | B01D 15/325 525/54.1 |

FOREIGN PATENT DOCUMENTS

| JP | S63-236539 A | 10/1988 |
|---|---|---|
| JP | H1-254247 A | 9/1998 |
| JP | 2006-095516 A | 4/2006 |
| JP | 2009-244067 A | 10/2009 |
| JP | 2014-521078 A | 8/2014 |
| WO | 2006/025556 A1 | 3/2006 |

OTHER PUBLICATIONS

Kai Li et al, "Synthesis of Monodisperse Poly (divinylbenzene) Microspheres," Journal of Polymer Science: Part A Polymer Chemistry, vol. 31,3257-3263 (1993).*

International Preliminary Report for WO Patent Appln. No. PCT/JP2016/051460 dated Aug. 3, 2017 with English translation.

International Search Report for PCT/JP2016/051460 dated Mar. 22, 2016; English translation submitted herewith (5 pages).

Qu Jian-Bo et al, "A novel stationary phase derivatized from hydrophilic gigaporous polystyrene-based microspberes for high-speed protein chromatography", Journal of Chromatography A, 2009, 1216, p. 6511-p. 6516.

Qu Jian-Bo et al, "An Effective Way to Hydrophilize Gigaporous Polystyrene Microspheres as Rapid Chromatographic Separation Media for Proteins", Langmuir, 2008, 24, p. I3646-p. I3652.

* cited by examiner

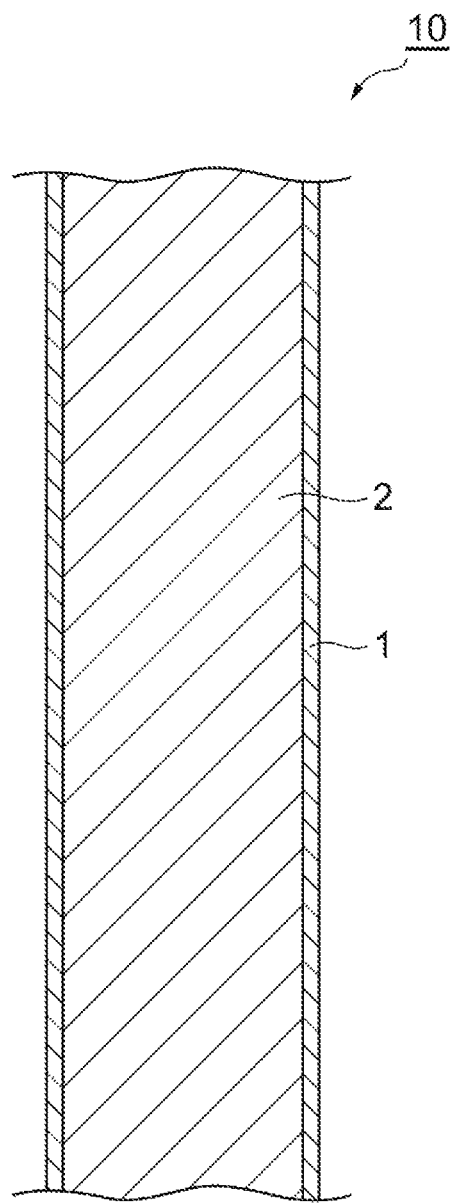

SEPARATION MATERIAL

CROSS-REFERENCE TO RELATED APPLICATIONS

This application is a U.S. national phase application filed under 35 U.S.C. § 371 of International Application PCT/JP2016/051460, filed on Jan. 19, 2016, designating the United States, which claims benefit of the filing dates of JP 2015-007776, filed Jan. 19, 2015, which is hereby incorporated herein by reference in its entirety.

TECHNICAL FIELD

The present invention relates to a separation material.

BACKGROUND ART

Conventionally, in a case in which bio-macromolecules that are represented by proteins are separated and purified, generally, an ion exchanger having a porous type synthetic macromolecule as a matrix, particles having a crosslinked gel of a hydrophilic natural macromolecule as a matrix, and the like are used. An ion exchanger having a porous type synthetic macromolecule as a matrix has an advantage that the pressure resistance is favorable at the time of liquid permeation. However, in a case in which this ion exchanger is used for the separation of a protein or the like, non-specific adsorption such as irreversible adsorption based on hydrophobic interaction occurs, and therefore, there is a problem that asymmetrization of peaks occurs, or a protein adsorbed to an ion exchanger by hydrophobic interaction remains adsorbed and cannot be collected.

Meanwhile, in the case of ion exchangers having crosslinked gels of hydrophilic natural macromolecules, which are represented by polysaccharides such as dextran and agarose as matrices, there is an advantage that non-specific adsorption of proteins hardly occurs. However, these ion exchangers have a defect that the ion exchangers swell conspicuously in aqueous solutions, undergo a large volume change due to the ionic strength of a solution and a large volume change between free acid type and load-sensitive type, and do not have sufficient mechanical strength. Particularly, in the case of using a crosslinked gel in chromatography, the ion exchangers have a defect that there is a high pressure loss at the time of liquid permeation, and the gel is consolidated as a result of liquid permeation.

In order to overcome a defect of having crosslinked gels of hydrophilic natural macromolecules, attempts have been hitherto made to combine rigid substances that serve as so-called skeletons.

For example, a composite in which a gel such as a natural macromolecule gel is retained within pores of a porous macromolecule is known in the field of peptide synthesis (see Patent Literature 1). It is described in Patent Literature 1 that by using such a composite, the load factor of a reactive substance is increased, and synthesis with high yield is enabled.

An ion exchanger of a hybrid copolymer, in which pores of a copolymer having a macro network structure are filled with a crosslinked copolymer gel synthesized from monomers, is known (see Patent Literature 2). A crosslinked copolymer gel has problems with pressure loss, volume change and the like in the case of having a low degree of crosslinking; however, it is described in Patent Literature 2 that by employing a hybrid copolymer, the liquid permeation characteristics are improved so that the pressure loss is decreased, and that the ion exchange capacity is increased while the leakage behavior is improved.

Compositized filler materials in which a crosslinked gel of a hydrophilic natural macromolecule having macro networks is filled in the pores of an organic synthetic macromolecule base, have been proposed (see Patent Literatures 3 and 4).

A technology of synthesizing porous particles that are composed of glycidyl methacrylate and an acrylic crosslinking monomer is known (see Patent Literature 5).

CITATION LIST

Patent Literature

Patent Literature 1: U.S. Pat. No. 4,965,289
Patent Literature 2: U.S. Pat. No. 3,966,489
Patent Literature 3: JP H01-254247 A
Patent Literature 4: U.S. Pat. No. 5,114,577
Patent Literature 5: JP 2009-244067 A

SUMMARY OF INVENTION

Technical Problem

In regard to conventional column packing materials, it is difficult to simultaneously address liquid permeability, which is a problem of natural macromolecules, and reduction of non-specific adsorption of proteins, increase in the adsorption amount, and suppression of degeneration, which are problems of polymer particles.

Thus, it is an object of the present invention to provide a separation material that secures liquid permeability and is capable of reducing non-specific adsorption of proteins, increasing the adsorption amount, and suppressing degeneration.

Solution to Problem

The present invention provides a separation material described in the following [1] to [6].

[1] A separation material comprising porous polymer particles that comprise at least one of styrene and divinylbenzene as a monomer unit at a proportion of 90% by mass or more based on the total amount of the monomers; and a coating layer that comprises a macromolecule having hydroxyl groups and covers at least a portion of the surface of the porous polymer particles, wherein the coating amount provided by the coating layer is 1 to 15 mg/m$^2$ per unit specific surface area of the porous polymer particles.

[2] The separation material according to [1], wherein the oxygen element ratio at the surface of the separation material is 10% to 50%.

[3] The separation material according to [1] or [2], wherein the macromolecule having hydroxyl groups is a polysaccharide or a modification product thereof.

[4] The separation material according to [3], wherein the polysaccharide is at least one selected from agarose, chitosan, alginic acid, and dextran.

[5] The separation material according to any one of [1] to [4], wherein the macromolecule having hydroxyl groups is crosslinked.

[6] The separation material according to any one of [1] to [5], wherein the specific surface area of the porous polymer particles is 10 m$^2$/g or more.

[7] The separation material according to any one of [1] to [6], wherein the mode diameter in the pore size distribution of the porous polymer particles is 0.05 to 1 μm.

[8] A separatory column comprising a column; and the separation material according to any one of [1] to [7] that is packed in the column.

Advantageous Effects of Invention

According to the present invention, a separation material that secures liquid permeability and is capable of reducing non-specific adsorption of proteins, increasing the adsorption amount, and suppressing degeneration, can be provided.

BRIEF DESCRIPTION OF DRAWINGS

FIG. 1 is a cross-sectional view illustrating an embodiment of a separatory column.

DESCRIPTION OF EMBODIMENTS

Hereinafter, suitable embodiments of the present invention will be described; however, the present invention is not intended to be limited to these embodiments.

<Separation Material>

The separation material of the present embodiment comprises porous polymer particles; and a coating layer that covers at least a portion of the surface of the porous polymer particles. In the present specification, the "surface of the porous polymer particles" is meant to include not only the external surface of the porous polymer particles, but also the surface of pores in the interior of the porous polymer particles.

(Porous Polymer Particles)

The porous polymer particles of the present embodiment are particles obtained by curing a monomer including a porosifier, and can be synthesized by, for example, conventional suspension polymerization and emulsion polymerization. Regarding the monomer unit, at least one of styrene and divinylbenzene is included at a proportion of 90% by mass or more based on the total amount of the monomers, and preferably, divinylbenzene is included at a proportion of 90% by mass or more based on the total amount of the monomers. When a predetermined amount of styrene or divinylbenzene is included, pressure resistance tends to be excellent.

The monomers may further include a polyfunctional monomer, a monofunctional monomer and the like, other than styrene and divinylbenzene, such as follows.

Examples of the polyfunctional monomer other than divinylbenzene include divinyl compounds such as divinylbiphenyl, divinylnaphthalene, and divinylphenanthrene. These polyfunctional monomers can be used singly or in combination of two or more kinds thereof.

Examples of the monofunctional monomer other than styrene include styrene derivatives such as o-methylstyrene, m-methylstyrene, p-methylstyrene, α-methylstyrene, o-ethylstyrene, m-ethylstyrene, p-ethylstyrene, 2,4-dimethylstyrene, p-n-butylstyrene, p-t-butylstyrene, p-n-hexylstyrene, p-n-octylstyrene, p-n-nonylstyrene, p-n-decylstyrene, p-n-dodecylstyrene, p-methoxystyrene, p-phenylstyrene, p-chlorostyrene, and 3,4-dichlorostyrene. These monofunctional monomers can be used singly or in combination of two or more kinds thereof. Furthermore, styrene derivatives having functional groups such as a carboxyl group, an amino group, a hydroxyl group and an aldehyde group, can also be used.

Examples of the porosifier include aliphatic or aromatic hydrocarbons, esters, ketones, ethers, and alcohols, which are organic solvents that accelerate phase separation at the time of polymerization and accelerate porosification of particles. Specific examples include toluene, xylene, diethylbenzene, cyclohexane, octane, butyl acetate, dibutyl phthalate, methyl ethyl ketone, dibutyl ether, 1-hexanol, 2-octanol, decanol, lauryl alcohol, and cyclohexanol. These porosifiers can be used singly or in combination of two or more kinds thereof.

The porosifier can be used in an amount of 0% to 200% by mass with respect to the total mass of the monomers. Porosity of the porous polymer particles can be controlled by the amount of the porosifier. Furthermore, the size and shape of the pores of the porous polymer particles can be controlled by the type of the porosifier.

Water that is used as a solvent can also be used as the porosifier. In a case in which water is used as the porosifier, porosification can be achieved by dissolving an oil-soluble surfactant in the monomer, and absorbing water.

Examples of the oil-soluble surfactant that is used for porosification include a sorbitan monoester of a branched C16-C24 fatty acid, a linear unsaturated C16-C22 fatty acid or a linear saturated C12-C14 fatty acid, for example, sorbitan monolaurate, sorbitan monooleate, sorbitan monomyristate, or a sorbitan monoester derived from coconut fatty acids; a diglycerol monoester of a branched C16-C24 fatty acid, a linear unsaturated C16-C22 fatty acid, or a linear saturated C12-C14 fatty acid, for example, diglycerol monooleate (for example, a diglycerol monoester of a C18:1 (number of carbon atoms: 18, number of double bonds: 1) fatty acid), diglycerol monomyristate, diglycerol monoisostearate, or diglycerol monoester of coconut fatty acids; a diglycerol monoaliphatic ether of a branched C16-C24 alcohol (for example, Guerbet alcohol), a linear unsaturated C16-C22 alcohol, or a linear saturated C12-C14 alcohol (for example, coconut fatty alcohol); and mixtures of these.

Among these, sorbitan monolaurate (for example, SPAN (registered trademark) 20; sorbitan monolaurate preferably having a purity of higher than about 40%, more preferably a purity of higher than about 50%, and most preferably a purity of higher than about 70%); sorbitan monooleate (for example, SPAN (registered trademark) 80; sorbitan monooleate preferably having a purity of higher than about 40%, more preferably a purity of about 50%, and most preferably a purity of higher than about 70%); diglycerol monooleate (for example, diglycerol monooleate preferably having a purity of higher than about 40%, more preferably a purity of higher than about 50%, and most preferably a purity of higher than about 70%); diglycerol monoisostearate (for example, diglycerol monoisostearate preferably having a purity of higher than about 40%, more preferably a purity of higher than about 50%, and most preferably a purity of higher than about 70%); diglycerol monomyristate (sorbitan monomyristate preferably having a purity of higher than about 40%, more preferably a purity of higher than about 50%, and most preferably a purity of higher than about 70%); cocoyl (for example, a lauryl group or a myristoyl group) ether of diglycerol; and mixtures of these, are preferred.

It is preferable to use these oil-soluble surfactants in an amount in the range of 5% to 80% by mass with respect to the total mass of the monomers. When the content of the oil-soluble surfactant is 5% by mass or more, since stability of water droplets becomes sufficient, it is difficult for large single holes to be formed. Furthermore, when the content of the oil-soluble surfactant is 80% by mass or less, it is easier for the porous polymer particles to maintain the shape after polymerization.

Examples of an aqueous medium that is used for the polymerization reaction include water, and a mixed medium of water and a water-soluble solvent (for example, a lower alcohol). The aqueous medium may include a surfactant. As the surfactant, among anionic, cationic, nonionic and zwitterionic surfactants, all can be used.

Examples of anionic surfactants include fatty acid oils such as sodium oleate and castor oil potassium; alkyl sulfuric acid ester salts such as sodium lauryl sulfate and ammonium lauryl sulfate; alkyl benzenesulfonic acid salts such as sodium dodecyl benzenesulfonate; alkyl naphthalenesulfonic acid salts; alkanesulfonic acid salts; dialkyl sulfosuccinic acid salts such as sodium dioctyl sulfosuccinate; alkenyl succinic acid salts (dipotassium salts); alkyl phosphoric acid ester salts; naphthalenesulfonic acid-formalin condensate, polyoxyethylene alkyl phenyl ether sulfuric acid ester salts; polyoxyethylene alkyl ether sulfuric acid salts such as sodium polyoxyethylene lauryl ether sulfate; and polyoxyethylene alkyl sulfuric acid ester salts.

Examples of cationic surfactants include alkyl amine salts such as lauryl amine acetate and stearyl amine acetate; and quaternary ammonium salts such as lauryl trimethylammonium chloride.

Examples of nonionic surfactants include hydrocarbon-based nonionic surfactants such as polyethylene glycol alkyl ethers, polyethylene glycol alkyl aryl ethers, polyethylene glycol esters, polyethylene glycol sorbitan esters, and polyalkylene glycol alkyl amines or amides; polyether-modified silicone-based nonionic surfactants such as polyethylene oxide adducts and polypropylene oxide adducts of silicones; and fluorine-based nonionic surfactants such as perfluoroalkyl glycols.

Examples of zwitterionic surfactants include hydrocarbon surfactants such as lauryl dimethylamine oxide; phosphoric acid ester-based surfactants, and phosphorous acid ester-based surfactants.

The surfactants may be used singly or in combination of two or more kinds thereof. Among the surfactants described above, from the viewpoint of dispersion stability at the time of monomer polymerization, anionic surfactants are preferred.

As a polymerization initiator that is added as necessary, for example, organic peroxides such as benzoyl peroxide, lauroyl peroxide, benzoyl orthochloroperoxide, benzoyl orthomethoxyperoxide, 3,5,5-trimethylhexanoyl peroxide, tert-butyl peroxy-2-ethylhexanoate, and di-tert-butyl peroxide; azo-based compounds such as 2,2'-azobisisobutyronitrile, 1,1'-azobiscyclohexanecarbonitrile, and 2,2'-azobis(2,4-dimethylvaleronitrile). The polymerization initiator can be used in an amount in the range of 0.1 to 7.0 parts by mass with respect to 100 parts by mass of the monomers.

The polymerization temperature can be appropriately selected according to the types of the monomer and the polymerization initiator. The polymerization temperature is preferably 25° to 110° C., and more preferably 50° C. to 100° C.

In regard to the synthesis of porous polymer particles, in order to enhance dispersion stability of the particles, a macromolecule dispersion stabilizer may also be used.

Examples of the macromolecule dispersion stabilizer include polyvinyl alcohol, polycarboxylic acids, celluloses (hydroxyethyl cellulose, carboxymethyl cellulose, methyl cellulose, and the like), polyvinylpyrrolidone, and inorganic water-soluble macromolecule compounds such as tricalcium phosphate (TCP) and sodium tripolyphosphate. These can be used singly or in combination of plural kinds thereof. Among these, tricalcium phosphate (TCP), polyvinyl alcohol or polyvinylpyrrolidone is preferred. The amount of addition of the macromolecule dispersion stabilizer is preferably 1 to 10 parts by mass with respect to 100 parts by mass of the monomers.

In order to prevent the monomers from being polymerized alone, water-soluble polymerization inhibitors such as nitrous acid salts, sulfurous acid salts, hydroquinones, ascorbic acids, water-soluble vitamins B compounds, citric acid, and polyphenols may also be used.

The average particle size of the porous polymer particles is preferably 300 μm or less, more preferably 150 μm or less, and even more preferably 100 μm or less. Furthermore, the average particle size of the porous polymer particles is preferably 10 μm or more, more preferably 30 μm or more, and even more preferably 50 μm or more, from the viewpoint of enhancing liquid permeability.

The coefficient of variation (C.V.) of the particle size of the porous polymer particles is preferably 3% to 15%, more preferably 5% to 15%, and even more preferably 5% to 10%, from the viewpoint of enhancing liquid permeability. As a method for reducing the C.V., a method of monodispersing the porous polymer particles by means of an emulsifying apparatus such as a MICRO PROCESS SERVER (manufactured by Hitachi, Ltd.) may be used.

The average particle size and the C.V. (coefficient of variation) of the particle size of the porous polymer particles or the separation material can be determined by the following measurement method.

1) Particles are dispersed in water (including a dispersant such as a surfactant) using an ultrasonic dispersing apparatus, and thus a dispersion liquid including 1% by mass of porous polymer particles is prepared.

2) The average particle size and the C.V. (coefficient of variation) of the particle size are measured from the images of about 10,000 particles in the dispersion liquid, using a particle size distribution meter (SYSMEX FLOW, manufactured by Sysmex Corp.).

The pore volume (porosity) of the porous polymer particles is preferably from 30% by volume to 70% by volume, and more preferably from 40% by volume to 70% by volume, based on the total volume (including the pore volume) of the porous polymer particles. It is preferable that the porous polymer particles have pores having a mode diameter in the pore size distribution (most frequent value of the pore size distribution, maximum frequency pore size, average pore size) of 0.05 to 1 μm. The mode diameter in the pore size distribution of the porous polymer particles is more preferably 0.2 μm or more and less than 0.5 μm. When the mode diameter in the pore size distribution is 0.05 μm or more, there is a tendency that substances can easily enter into the pores, and when the mode diameter in the pore size distribution is less than 1 μm, the specific surface area becomes sufficient. These can be adjusted by means of the porosifier mentioned above.

The specific surface area of the porous polymer particles is preferably 10 m$^2$/g or more, and more preferably 30 m$^2$/g or more. From the viewpoint of higher practical usability, the specific surface area is more preferably 35 m$^2$/g or more, and even more preferably 40 m$^2$/g or more. When the specific surface area is 10 m$^2$/g or more, the adsorption amount of the substance to be separated tends to increase. The upper limit of the specific surface area of the porous polymer particles is not particularly limited; however, for example, the specific surface area can be adjusted to be 200 m²/g or less, and 100 m²/g or less.

(Coating Layer)

The coating layer of the present embodiment comprises a predetermined amount (coating amount) of a macromolecule having hydroxyl groups. When the porous polymer particles are coated with a predetermined amount of a macromolecule having hydroxyl groups, increase in the column pressure can be suppressed, non-specific adsorption of proteins can also be suppressed, and the protein adsorption amount of the separation material tends to improve. Furthermore, when the macromolecule having hydroxyl groups is crosslinked, the increase in the column pressure can be further suppressed.

The separation material of the present embodiment is such that the coating amount provided by the coating layer is 1 to 15 mg/m², preferably 5 to 15 mg/m², and more preferably 8 to 15 mg/m², per unit specific surface area of the porous polymer particles. When the coating amount provided by the coating layer is adjusted to a predetermined range, suppression of non-specific adsorption and protein degeneration as well as an increase in the adsorption amount in the case of being used as a separation material for a protein, are made possible. The coating amount provided by the coating layer can be measured by the method described in Examples, or the like.

The separation material of the present embodiment is such that the oxygen element ratio at the surface thereof is preferably 10% to 50%, more preferably 15% to 50%, even more preferably 20% to 50%, and particularly preferably 30% to 50%. By adjusting the oxygen element ratio at the surface of the separation material to a predetermined range, the effect of suppressing non-specific adsorption and protein degeneration and the effect of increasing the adsorption amount in the case of being used as a separation material for a protein, are further enhanced. The oxygen element ratio at the surface of the separation material can be measured by the method described in Examples or the like. The oxygen element ratio at the surface of the separation material is measured by X-ray photoelectron spectroscopy, by which the coating layer is irradiated with X-radiation from the external side of the separation material.

(Macromolecule Having Hydroxyl Group)

It is preferable that the macromolecule having hydroxyl groups has two or more hydroxyl groups in one molecule, and it is more preferable that the macromolecule having hydroxyl groups is a hydrophilic macromolecule. Examples of the macromolecule having hydroxyl groups include polysaccharides and polyvinyl alcohol. Preferred examples of the polysaccharides include agarose, dextran, cellulose, chitosan, and alginic acid. As the macromolecule having hydroxyl groups, for example, a macromolecule having a weight average molecular weight of about 10,000 to 200,000 can be used.

It is preferable that the macromolecule having hydroxyl groups is a modification product that has been modified with a hydrophobic group, from the viewpoint of enhancing the interface adsorption capacity. Examples of the hydrophobic group include an alkyl group having 1 to 6 carbon atoms, and an aryl group having 6 to 10 carbon atoms. Examples of the alkyl group having 1 to 6 carbon atoms include a methyl group, an ethyl group, and a propyl group. Examples of the aryl group having 6 to 10 carbon atoms include a phenyl group and a naphthyl group. A hydrophobic group can be introduced by causing a compound that has a functional group which reacts with a hydroxyl group (for example, an epoxy group) and has a hydrophobic group (for example, glycidyl phenyl ether), to react with the macromolecule having hydroxyl groups by a conventionally known method.

(Method for Forming Coating Layer)

The coating layer that comprises a macromolecule having hydroxyl groups can be formed by, for example, a method disclosed below.

First, a solution of a macromolecule having hydroxyl groups is adsorbed onto the surface of porous polymer particles. The solvent for the solution of a macromolecule having hydroxyl groups is not particularly limited as long as the solvent can dissolve the macromolecule having hydroxyl groups; however, water is most general. The concentration of the macromolecule that is dissolved in the solvent is preferably 5 to 20 (mg/mL).

This solution is impregnated into the porous polymer particles. Regarding the method for impregnation, the porous polymer particles are added to the solution of a macromolecule having hydroxyl groups, and the solution is left to stand for a certain time. The impregnation time may vary depending on the surface state of the porous body; however, usually, when impregnation is carried out for one day and one night, the polymer concentration in the interior of the porous body reaches an equilibrium state with the external concentration. Subsequently, the porous body is washed with a solvent such as water or an alcohol, and any unadsorbed portion of the macromolecule having hydroxyl groups is removed.

(Crosslinking Treatment)

Next, a crosslinking agent is added thereto, and the macromolecule having hydroxyl groups that has adsorbed onto the surface of the porous polymer particles is subjected to a crosslinking reaction. Thus, a crosslinked product is formed. That is, the macromolecule having hydroxyl groups of the separation material may be crosslinked. At this time, the crosslinked product has a three-dimensionally crosslinked network structure having hydroxyl groups.

Examples of the crosslinking agent include compounds each having two or more functional groups that are active on a hydroxyl group, such as epihalohydrins such as epichlorohydrin; dialdehyde compounds such as glutaraldehyde; diisocyanate compounds such as methylene diisocyanate; and glycidyl compounds such as ethylene glycol diglycidyl ether. Furthermore, in a case in which a compound having amino groups, such as chitosan, is used as the macromolecule having hydroxyl groups, a dihalide such as dichlorooctane can also be used as the crosslinking agent.

For this crosslinking reaction, a catalyst is usually used. Regarding the catalyst, a conventionally known catalyst can be used as appropriate in accordance with the type of the crosslinking agent; however, for example, in a case in which the crosslinking agent is epichlorohydrin, an alkali such as sodium hydroxide is effective, and in the case of a dialdehyde compound, a mineral acid such as hydrochloric acid is effective.

The crosslinking reaction by a crosslinking agent is usually carried out by adding a crosslinking agent to a system in which the separation material has been dispersed and suspended in an appropriate medium. Regarding the amount of addition of the crosslinking agent, in a case in which a polysaccharide is used as the macromolecule having hydroxyl groups, when one unit of a monosaccharide is regarded as one mole, the amount of addition can be selected according to the performance of the separation material, for example, within the range of 0.1 to 100 times the molar amount of the monosaccharide. Generally, when the amount of addition of the crosslinking agent is reduced, there is a tendency that the coating layer is easily detached from the porous polymer particles. Furthermore, in a case in which the amount of addition of the crosslinking agent is in excess, and the reaction ratio with the macromolecule having hydroxyl groups is high, the characteristics of the macromolecule having hydroxyl groups as a raw material tend to be impaired.

The amount of use of the catalyst may vary with the type of the crosslinking agent; however, usually in a case in which a polysaccharide is used as the macromolecule having hydroxyl groups, when one unit of the monosaccharide that forms the polysaccharide is regarded as one mole, the catalyst is used preferably in an amount in the range of 0.01 to 10 times, and more preferably 0.1 to 5 times, the molar amount of this monosaccharide.

For example, when temperature conditions are employed as the crosslinking reaction conditions, when the temperature of the reaction system is raised, and the temperature reaches the reaction temperature, a crosslinking reaction occurs.

The medium in which the porous polymer particles that have been impregnated with a solution of a macromolecule having hydroxyl groups are dispersed and suspended, needs to be a medium which does not extract a macromolecule, a crosslinking agent and the like from the macromolecule solution that has been impregnated, and is inactive to the crosslinking reaction. Specific examples of the medium include water, an alcohol, toluene, dichlorobenzene, and nitromethane.

The crosslinking reaction is usually carried out at a temperature in the range of 5° C. to 90° C. for 1 to 10 hours. Preferably, the reaction is carried out at a temperature in the range of 30° C. to 90° C.

After completion of the crosslinking reaction, when the particles thus produced are separated by filtration and then washed with water. Or a hydrophilic organic solvent such as methanol or ethanol, and any unreacted macromolecule, the medium for suspending, and the like are removed, a separation material in which at least a portion of the surface of porous polymer particles is covered by a coating layer comprising a macromolecule having hydroxyl groups is able to be obtained.

(Introduction of Ion Exchanging Group)

The separation material that comprises a coating layer can be used for ion exchange purification, affinity purification and the like, by introducing an ion exchanging group, a ligand (Protein A) or the like via a hydroxyl group or the like on the surface. As a method for introducing an ion exchanging group, for example, a method of using a halogenated alkyl compound may be mentioned.

Examples of the halogenated alkyl compound include a monohalogenocarboxylic acid such as a monohalogenoacetic acid or a monohalogenopropionic acid, and a sodium salt thereof; a primary, secondary or tertiary amine having at least one halogenated alkyl group, such as diethylaminoethyl chloride; and hydrochloride of a quaternary ammonium having a halogenated alkyl group. These halogenated alkyl compounds are preferably bromides or chlorides. The amount of use of the halogenated alkyl compound is preferably 0.2% by mass or more with respect to the total mass of the separation material to which an ion exchanging group is imparted.

For the introduction of an ion exchanging group, it is effective to use an organic solvent in order to accelerate the reaction. Examples of the organic solvent include alcohols such as ethanol, 1-propanol, 2-propanol, 1-butanol, isobutanol, 1-pentanol, and isopentanol.

Since the introduction of an ion exchanging group is usually carried out into a hydroxyl group on the separation material surface, particles in a wet state are dehydrated by filtration or the like, and then the particles are immersed in an alkaline aqueous solution at a predetermined concentration and are left to stand for a certain time. Subsequently, the halogenated alkyl compound is added and reacted in a water-organic solvent mixed system. It is preferable that this reaction is performed at a temperature of 40° C. to 90° C. for 0.5 to 12 hours. The ion exchanging group to be provided is determined based on the type of the halogenated alkyl compound used for the above-described reaction.

As a method for introducing an amino group, which is a weakly basic group, as the ion exchanging group, a method of reacting, among the above-mentioned halogenated alkyl compounds, a mono-, di- or trialkylamine, a mono-, di- or trialkanolamine, a mono-alkyl-mono-alkanolamine, a di-alkyl-mono-alkanolamine, a mono-alkyl-di-alkanolamine, or the like, all of which have at least one alkyl group in which some of hydrogen atoms have been substituted by chlorine atoms, may be mentioned. The amount of use of these halogenated alkyl compounds is preferably 0.2% by mass or more with respect to the total mass of the separation material. The reaction conditions are preferably 40° C. to 90° C. and 0.5 to 12 hours.

As a method for introducing a quaternary ammonium group, which is a strongly basic group, as the ion exchanging group, a method of first introducing a tertiary amino group, reacting the tertiary amino group with a halogenated alkyl compound such as epichlorohydrin, and converting the tertiary amino group into a quaternary ammonium group, may be mentioned. Furthermore, hydrochloride of a quaternary ammonium or the like may also be reacted with the separation material.

As a method for introducing a carboxyl group, which is a weakly acidic group, as the ion exchanging group, a method of reacting a monohalogenocarboxylic acid such as a monohalogenoacetic acid or a monohalogenopropionic acid, or a sodium salt thereof as the halogenated alkyl compound, may be mentioned. The amount of use of these halogenated alkyl compounds is preferably 0.2% by mass or more with respect to the total mass of the separation material into which the ion exchanging group is introduced.

As a method for introducing a sulfonic acid group, which is a strongly acidic group, as the ion exchanging group, a method of reacting the separation material with a glycidyl compound such as epichlorohydrin, and adding the separation material to a saturated aqueous solution of a sulfurous acid salt or a bisulfurous acid salt, such as sodium sulfite or sodium bisulfite, may be mentioned. The reaction conditions are preferably 30° C. to 90° C. and 1 to 10 hours.

Meanwhile, as a method for introducing an ion exchanging group, a method of reacting the separation material with 1,3-propanesultone in an alkaline atmosphere may also be mentioned. It is preferable to use 1,3-propanesultone in an amount of 0.4% by mass or more with respect to the total mass of the separation material. The reaction conditions are preferably 0° C. to 90° C. and 0.5 to 12 hours.

The degree of hygroscopicity of the separation material of the present embodiment is measured by the following method. 1 g of a dry separation material is left to stand for 18 hours in a constant temperature constant humidity test chamber (temperature 60° C., humidity 90%), and then the mass of the separation material is measured again. Thereby, the degree of hygroscopicity is calculated by the following formula.

(Separation material mass after moisture absorption−1)g/1g×100=Degree of hygroscopicity (%)

The degree of hygroscopicity of the separation material of the present embodiment is preferably 1% to 30% by mass, more preferably 1% to 20% by mass, and even more preferably 1% to 10% by mass. When the degree of hygroscopicity of the separation material is 30% by mass or less, the decrease in liquid permeability of the separation material due to the thickness of the coating layer can be suppressed.

The average pore size, the mode diameter in the pore size distribution, the specific surface area, and the porosity of the separation material or porous polymer particles of the present embodiment are values measured with a mercury intrusion analyzer (AUTOPORE; manufactured by Shimadzu Corp.), and these are measured as follows. 0.05 g of a sample is added to a standard 5-mL cell for powder (stem volume 0.4 mL), and measurement is made under the conditions of an initial pressure of 21 kPa (about 3 psia, equivalent to a pore diameter of about 60 μm). The mercury parameter is set to have a mercury contact angle of 130 degrees, which is an apparatus default value, and a mercury surface tension of 485 dynes/cm. Furthermore, the respective values are calculated with limiting the pore size to the range of 0.1 to 3 μm.

The separation material of the present embodiment is suitable for the use in separation of a protein by electrostatic interaction and affinity purification. For example, when the separation material of the present embodiment is added to a mixed solution including a protein, only the protein is adsorbed onto the separation material by electrostatic interaction, and then the separation material is separated by filtration from the solution and is added to an aqueous solution having a high salt concentration, the protein that has adsorbed to the separation material can be easily released and collected. Furthermore, the separation material of the present embodiment can also be used for column chromatography. An embodiment of a separatory column is illustrated in FIG. 1. The separatory column 10 comprises a column 1 and a separation material 2 packed in the column 1.

As a bio-macromolecule that can be separated by using the separation material of the present embodiment, a water-soluble substance is preferred. Specific examples include proteins, such as blood proteins such as serum albumin and immunoglobulin; enzymes present in the living body; protein physiologically active substances produced by biotechnologies; and bio-macromolecules such as DNA and physiologically active peptides. The weight average molecular weight is preferably 2,000,000 or less, and more preferably 500,000 or less. Furthermore, it is necessary to select, according to known methods, the properties of the separation material, conditions and the like based on the isoelectric point, ionization state and the like of the protein. As the known methods, for example, the method described in JP S60-169427 A may be mentioned.

The separation material of the present embodiment has the respective advantages of particles formed from a natural macromolecule or particles formed from a synthetic macromolecule in connection with the separation of a bio-macromolecule such as a protein, by subjecting the coating layer on the porous polymer particles to a crosslinking treatment, and then introducing an ion exchanging group, Protein A or the like into the surface of the separation material. Particularly, since the porous polymer particles in the separation material of the present embodiment are particles that are obtained by the method described above, the porous polymer particles have durability and alkali resistance. Furthermore, the separation material of the present embodiment has a tendency that non-specific adsorption of proteins is reduced, and adsorption and desorption of proteins easily occurs. Furthermore, the separation material of the present embodiment has a tendency that the adsorption amount of a protein or the like under the same flow rate (dynamic adsorption amount) is large.

The liquid permeation rate according to the present specification represents the liquid permeation rate at the time when the separation material of the present embodiment is packed in a stainless steel column having a size of $\phi$ 7.8×300 mm, and a liquid is passed therethrough. In a case in which the separation material of the present embodiment is packed in a column, it is preferable that when the column pressure is 0.3 MPa, the liquid permeation rate is 800 cm/h or higher. In a case in which separation of a protein is performed by column chromatography, the liquid permeation rate of a protein solution or the like is generally in the range of 400 cm/h or less; however, in a case in which the separation material of the present embodiment is used, the separation material can be used at a liquid permeation rate of 800 cm/h or higher, which is faster than those of conventional separation materials for protein separation.

The average particle size of the separation material of the present embodiment is preferably 10 to 300 μm. For the use in preparative or industrial chromatography, in order to avoid an extreme increase in the column internal pressure, the average particle size is preferably 10 to 100 μm.

In a case in which the separation material of the present embodiment is used as a column packing material in column chromatography, since there is hardly any volume change within the column independently of the properties of the eluent used, operability is excellent.

The 5% compressive deformation modulus of the separation material of the present embodiment can be calculated as follows.

The load and compression displacement at the time when particles are compressed up to 50 mN by means of a smooth cross-section (50 μm×50 μm) of a quadrangular prism at a load loading rate of 1 mN/sec under the conditions of room temperature (25° C.), by using a microcompression testing machine (manufactured by Fisher Scientific Co., LLC). The compression modulus (5% K value) at the time when the particles have undergone 5% compressive deformation can be determined from the measurement values thus obtained, by the formula described below. The load at the point where the amount of displacement undergoes the largest change during the measurement is designated as the breaking strength (mN).

5% $K$ value (MPa)=$(3/2^{1/2})\cdot F \cdot S^{-3/2} \cdot R^{-1/2}$

F: Load (mN) at the time when crosslinked polymer particles have undergone 40% compressive deformation S: Compression displacement (mm) at the time when crosslinked polymer particles have undergone 40% compressive deformation R: Radius (mm) of crosslinked polymer particles The compression modulus (5% K value) at the time when the separation material is subjected to 5% compressive deformation is preferably 100 to 1,000 MPa, more preferably 200 to 1,000 MPa, and even more preferably 250 to 1,000 MPa.

The pore volume (porosity) of the separation material is preferably from 30% by volume to 70% by volume, and more preferably from 40% by volume to 70% by volume, based on the total volume (including the pore volume) of the separation material. It is preferable that the separation material has pores having an average pore size of 0.05 to 1 µm. The average pore size is preferably 0.2 to 0.5 µm. When the pore size is 0.05 µm or more, there is a tendency that substances can easily enter into the pores, and when the pore size is 1 µm or less, the specific surface area becomes sufficient.

The specific surface area of the separation material is preferably 10 $m^2/g$ or more, and more preferably 30 $m^2/g$ or more. From the viewpoint of higher practical usability, the specific surface area is more preferably 35 $m^2/g$ or more, and even more preferably 40 $m^2/g$ or more. When the specific surface area is 10 $m^2/g$ or more, the adsorption amount of the substance to be separated tends to increase.

The 5% deformation modulus, the mode diameter in the pore size distribution, the specific surface area and the like of the separation material can be adjusted by appropriately selecting the ingredients of the porous polymer particles, the porosifier, the macromolecule having hydroxyl groups, and the like.

In the present embodiment, a separation material in the form of having an ion exchanging group introduced thereinto has been explained; however, even if an ion exchanging group is not introduced, the separation material can be used as a separation material. Such a separation material can be utilized in, for example, gel permeation chromatography. That is, a separatory column of the present embodiment comprises a column and the separation material of the present embodiment packed in the column.

EXAMPLES

Hereinafter, the present invention will be described by way of Examples; however, the present invention is not intended to be limited to these Examples.

Example 1

<Synthesis of Porous Polymer Particles>

16 g of divinylbenzene (manufactured by Nippon Steel & Sumikin Chemical Co., Ltd., trade name: DVB960) having a purity of 96%, 19.5 g of isoamyl alcohol, 4.5 g of diethylbenzene, and 0.64 g of benzoyl peroxide were introduced into a 500-mL three-necked flask, and an aqueous solution of tricalcium phosphate (TCP) (0.5% by mass) was prepared. This aqueous solution was emulsified by using a MICRO PROCESS SERVER, subsequently the emulsion liquid thus obtained was transferred into a flask, and the emulsion liquid was stirred for about 8 hours by using a stirrer, while being heated in a water bath at 80° C. The particles thus obtained were filtered, and then washed with acetone. Lastly, TCP was dissolved in an acidic aqueous solution, and thus, porous polymer particles 1 were obtained. The specific surface area and the mode diameter in the pore size distribution of the particles thus obtained, were measured by a mercury intrusion method, and the average particle size of the particles was measured with a flow type particle size analyzer. The results are presented in Table 1.

<Formation and Crosslinking of Coating Layer>

4 g of sodium hydroxide and 0.14 g of glycidyl phenyl ether were introduced into 100 mL of an aqueous solution of agarose (2% by mass), and the mixture was reacted for 12 hours at 70° C. Thus, phenyl groups were introduced into agarose. The modified agarose thus obtained was reprecipitated with isopropyl alcohol, and was washed.

The porous polymer particles 1 were introduced into a 200 mg/mL aqueous solution of the modified agarose at a proportion of 1 g of the porous polymer particles 1 in 70 mL of the aqueous solution, and the mixture was stirred for 24 hours at 50° C. Thereby, the modified agarose was adsorbed onto the porous polymer particles 1. After adsorption, the porous polymer particles were filtered and washed with hot water for 8 hours. The results are presented in Table 1.

The modified agarose was crosslinked as follows. The porous polymer particles 1 with the modified agarose adsorbed thereto were introduced into an aqueous solution in which the concentrations of ethylene glycol diglycidyl ether and sodium hydroxide were 0.64 M and 0.4 M, respectively, at a proportion of 1 g of the particles were introduced into 35 mL of the aqueous solution, and the mixture was stirred for 24 hours at room temperature. Subsequently, the resultant was washed with a heated 2 mass % aqueous solution of sodium dodecyl sulfate, subsequently washed with pure water, and dried. Thus, a separation material was obtained.

(Measurement of Coating Amount Provided by Modified Agarose on Porous Polymer Particles)

For the measurement of the adsorption amount of agarose onto the porous polymer particles, an analysis based on weight reduction caused by thermal decomposition was performed. 10 mg each of the porous polymer particles, the modified agarose, and the particles (separation material) obtained by the formation and crosslinking of the coating layer were heated from 30° C. to 900° C. Since it was known that the porous polymer particles is thermally decomposed at 500° C., and the modified agarose is thermally decomposed at 300° C., the modified agarose coating amount of the modified agarose-coated porous polymer particles was calculated from these two data.

Specifically, the weight reductions of the modified agarose and the porous polymer particles were measured by a thermogravimetric analysis, and the amount of the modified agarose per 1 g of the porous polymer particles was calculated. Here, the amount of the modified agarose per 1 g of the porous polymer particles thus calculated was divided by the specific surface area, and thereby the coating amount per unit specific surface area was calculated (see the following formula (1)). The results are presented in Table 1.

Coating amount per unit specific surface area [mg/$m^2$]=(Amount of weight reduction of macromolecule having hydroxyl groups [%])/(amount of weight reduction of porous polymer particles [%])/specific surface area [$m^2/g$])×1000   Formula (1)

(Evaluation of Non-Specific Adsorption Ability for Protein)

First, a calibration curve was produced (0 to 0.4%) with aqueous solutions of BSA (bovine serum albumin) at known concentrations. 200 mg of the particles (separation material) obtained according to the "formation and crosslinking of coating layer" were immersed in water at 20° C. for 12 hours, and the particles were caused to swell. The swollen particles and 10 mL of water were weighed in a vial. BSA was weighed in a 100-mL measuring flask, and was dissolved in a phosphate saline buffer solution (pH=7.1). Thus, aqueous solutions of BSA at 12 mg/mL and 24 mg/mL were prepared. 10 mL each of these BSA solutions were added to the particle solution described above, and the mixtures were stirred with a mix rotor for 24 hours at 25° C. 10 mL of the supernatant of this solution was diluted 10 times, and the absorbance (280 nm) was measured. Thus, the BSA adsorption amount to the separation material was calculated as the non-specific adsorption amount. The results are presented in Table 2.

(Measurement of Oxygen Element Ratio)

The particles (separation material) obtained by the "formation and crosslinking of coating layer" were dried for 12 hours at 70° C. in a dryer, and then the oxygen element ratio of the particle surface was measured with an XPS (X-ray photoelectron spectroscopy) apparatus as described below. The results are presented in Table 1.

Furthermore, after the particles were dried by a same method, the particles were mashed with a mortar, and the oxygen element ratio in the interior of the particles was measured with an XPS apparatus as described below. The results are presented in Table 1.

Meanwhile, the oxygen element ratio was calculated by dividing the intensity of the peak originating from oxygen element by the intensity of the peak of an element other than hydrogen element.

XPS apparatus: PHI 5000 VersaProbeII manufactured by Ulvac PHI, Inc.

X-radiation: monochromatized Alkα radiation (1486.6 eV)

Analyzed area: 200 μm$^2$

Analyzed depth: 50 Å

<Introduction of Ion Exchanging Group>

The particles (separation material) obtained by the "formation and crosslinking of coating layer" were centrifuged to remove water, and then the particles were introduced into a liquid prepared by mixing 20 mL of a 5 M aqueous solution of sodium hydroxide and 20 mL of a 5 M aqueous solution of diethylaminoethyl hydrochloride. The mixture was stirred for 12 hours at 70° C. After completion of the reaction, the particles are filtered and washed with water, and thus a DEAE-modified separation material having a diethylaminoethyl (DEAE) group as an ion exchanging group was obtained.

(Evaluation of Protein Binding Capacity and Recovery Rate)

200 mg of the DEAE-modified separation material thus obtained was immersed in water at 20° C. for 12 hours and was caused to swell. The swollen separation material and 10 mL of water were weighed in a vial. Bovine serum albumin (BSA) was weighed in a 100-mL measuring flask, and was dissolved in a phosphate saline buffer solution (pH=7.1). Thus, aqueous solutions of BSA at 1.2 mg/mL and 12 mg/mL were prepared. 10 mL of this BSA solution was added to the vial, with which the swollen separation material had been weighed, and the mixture was stirred with a mix rotor for 24 hours at 25° C. 10 mL of the supernatant of this solution was diluted 10 times, and the absorbance (280 nm) was measured. Thus, the BSA adsorption amount (binding capacity) to the DEAE-modified separation material was calculated. The results are presented in Table 2.

0.9 g of NaCl was added to this vial, and the mixture was stirred with a mix rotor for 12 hours at 25° C. 5 mL of the supernatant of this solution was diluted 10 times, and the absorbance (280 nm) was measured. The BSA recovery rate by the separation material was calculated as shown by formula (2). The results are presented in Table 2.

Protein recovery rate=(Absorbance after protein desorption−absorbance before protein desorption)/(absorbance after protein adsorption−absorbance before protein adsorption)    Formula (2)

(Method for Quantitatively Determining Ion Exchanging Group)

0.2 to 0.3 g of the DEAE-modified separation material that had been swollen with water for 12 hours or longer was precisely weighed, and was transferred into a beaker. 20 mL of a 0.1 N sodium hydroxide solution was introduced thereinto, and the content was stirred. Subsequently, suction filtering was performed, and the particles on the filter were washed until the washing liquid became neutral. Subsequently, the particles were transferred into a beaker, 20 mL of a 0.1 N aqueous solution of hydrochloric acid was added thereto, and the mixture was stirred for 1 hour at room temperature. Subsequently, suction filtering was performed, and the particles on the filter were washed until the washing liquid became neutral. This washing liquid was titrated with a 0.1 N aqueous solution of sodium hydroxide by using an automatic potential difference titration apparatus, and the ion exchange capacity was measured. The results are presented in Table 2.

(Evaluation of Column Characteristics)

The DEAE-modified separation material thus obtained was packed in a stainless steel column having a size of ϕ 7.8×300 mm as a slurry (solvent: methanol) having a concentration of 30% by mass over 15 minutes. Subsequently, water was caused to flow through the column while the flow rate was varied, and the relation between the linear flow rate and the column pressure was measured. Thus, the linear flow rate (liquid permeation rate) at 0.3 MPa was measured. The results are presented in Table 1.

Example 2

Synthesis and evaluation were carried out in the same manner as in Example 1, except that for the <Formation and crosslinking of coating layer>, epichlorohydrin was used instead of ethylene glycol diglycidyl ether.

Example 3

Synthesis and evaluation were carried out in the same manner as in Example 2, except that for the <Synthesis of porous polymer particles>, the amounts of use of isoamyl alcohol and diethylbenzene were changed to 16 g and 8 g, respectively.

Comparative Example 1

The porous polymer particles 1 as it is were used without any modification, and were evaluated in the same manner as in Example 1.

Comparative Example 2

Synthesis and evaluation were carried out in the same manner as in Example 1, except that for the <Formation and crosslinking of coating layer>, the concentration of the aqueous solution of the modified agarose was changed to 20 mg/mL.

Comparative Example 3

Commercially available agarose particles (Capto DEAE; GE Healthcare Co.) were used as Comparative Example 3, and were evaluated in the same manner as in Example 1.

TABLE 1

| Item | Average particle size (μm) | Mode diameter in pore size distribution (μm) | Specific surface area (m²/g) | Linear flow rate (cm/h) at 0.3 MPa | Coating amount (mg/m²) | Oxygen element ratio at particle surface (%) | Oxygen element ratio in interior of particles (%) |
|---|---|---|---|---|---|---|---|
| Example 1 | 95 | 0.3 | 28 | 1100 | 1.6 | 29 | 18 |
| Example 2 | 95 | 0.3 | 28 | 1100 | 4.5 | 29 | 18 |
| Example 3 | 95 | 0.1 | 73 | 1500 | 8.1 | 35 | 30 |
| Comparative Example 1 | 95 | 0.3 | 28 | 1100 | 0 | 7 | 3 |
| Comparative Example 2 | 95 | 0.3 | 28 | 1100 | 0.3 | 29 | 5 |
| Comparative Example 3 | 98 | 0.15 | — | 750 | — | 35 | 35 |

TABLE 2

| Item | Ion exchange capacity (mmol/mL) | Non-specific adsorption amount (mg/mL of particles) | Protein binding capacity (mg/mL of particles) | Protein recovery rate (%) |
|---|---|---|---|---|
| Example 1 | 0.08 | 1 or less | 73 | 83 |
| Example 2 | 0.21 | 1 or less | 83 | 90 |
| Example 3 | 0.30 | 1 or less | 91 | 95 |
| Comparative Example 1 | 0 | 180 | 0 | 0 |
| Comparative Example 2 | 0.05 | 180 | 0 | 0 |
| Comparative Example 3 | 0.26 | 1 or less | 61 | 80 |

As is obvious from Table 1, when a comparison is made between the linear flow rate of the case in which the synthetic polymer particles of Examples 1, 2 and 3 and Comparative Examples 1 and 2 were used, and the linear flow rate of the case in which the agarose particles of Comparative Example 1 were used, the synthetic polymer particles had high and favorable liquid permeability. However, when coating with a macromolecule having hydroxyl groups was not implemented, a large amount of non-specific adsorption occurred and proteins were degenerated, as in the case of Comparative Example 1. In Comparative Example 2, the coating amount provided by the macromolecule having hydroxyl groups was reduced. In this case as well, similarly to Comparative Example 1, a large amount of non-specific adsorption occurred, and proteins were degenerated. In Example 1, the coating amount provided by the macromolecule having hydroxyl groups was adjusted to be in the predetermined range of the present invention. Thereby, suppression of non-specific adsorption and protein degeneration was enabled, and the protein binding capacity and the protein recovery rate were enhanced compared to the case of using agarose particles. Furthermore, in Example 2, the crosslinking agent was changed from that of Example 1. In Example 2, non-specific adsorption and protein degeneration were suppressed similarly to Example 1, the ion exchange capacity was further increased, and the protein binding capacity was enhanced. In Example 3, the coating amount per unit specific surface area of the particles was increased compared to Example 2. In Example 3, non-specific adsorption and protein degeneration were suppressed similarly to Example 2, the ion exchange capacity was further increased, and the protein binding capacity and the protein recovery rate were enhanced to large extents.

REFERENCE SIGNS LIST

1 . . . Column, 2 . . . Separation material, 10 . . . Separatory column.

The invention claimed is:

1. A separation material comprising:
   porous polymer particles that comprise divinylbenzene as a monomer unit at a proportion of 90% by mass or more based on the total amount of monomers; and
   a coating layer that comprises a cross-linked modified agarose and covers at least a portion of the surface of the porous polymer particles,
   wherein the coating amount provided by the coating layer per unit specific surface area of the porous polymer particles is 4.5 to 15 mg/m².

2. The separation material according to claim 1, wherein the oxygen element ratio at the surface of the separation material is 10% to 50%.

3. The separation material according to claim 1, wherein a specific surface area of the porous polymer particles is 10 m²/g or more.

4. The separation material according to claim 1, wherein the mode diameter in the pore size distribution of the porous polymer particles is 0.05 to 1 μm.

5. A separatory column comprising a column; and the separation material according to claim 1 that is packed in the column.

6. The separation material according to claim 1, wherein the cross-linked modified agarose is a cross-linked phenyl modified agarose.

7. The separation material according to claim 6, wherein the cross-linked phenyl modified agarose is cross-linked with epichlorohydrin.

8. The separation material according to claim 7, wherein an amount of the cross-linked phenyl modified agarose cross-linked with epichlorohydrin per unit specific surface area of the porous polymer particles is 4.5 to 15 mg/m².

9. The separation material according to claim 6, wherein an amount of the cross-linked phenyl modified agarose per unit specific surface area of the porous polymer particles is 4.5 to 15 mg/m².

10. The separation material according to claim 1, wherein an amount of the cross-linked modified agarose per unit specific surface area of the porous polymer particles is 4.5 to 15 mg/m².

* * * * *